United States Patent
Vanderveen et al.

(10) Patent No.: US 9,415,175 B2
(45) Date of Patent: Aug. 16, 2016

(54) SYSTEM AND METHOD FOR VERIFYING ALIGNMENT OF DRUG PUMP AND FLUID SUPPLY

(71) Applicant: CareFusion 303, Inc., San Diego, CA (US)

(72) Inventors: Timothy Vanderveen, San Diego, CA (US); Stephen Bollish, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 704 days.

(21) Appl. No.: 13/842,146

(22) Filed: Mar. 15, 2013

(65) Prior Publication Data

US 2014/0276575 A1 Sep. 18, 2014

(51) Int. Cl.
*A61M 5/50* (2006.01)
*A61M 5/142* (2006.01)
*A61M 5/168* (2006.01)
*A61M 1/36* (2006.01)

(52) U.S. Cl.
CPC .......... *A61M 5/5086* (2013.01); *A61M 5/142* (2013.01); *A61M 5/16827* (2013.01); *A61M 5/16854* (2013.01); *A61M 1/365* (2014.02); *A61M 1/3643* (2013.01); *A61M 5/14228* (2013.01); *A61M 5/16859* (2013.01); *A61M 2205/14* (2013.01); *A61M 2205/3355* (2013.01)

(58) Field of Classification Search
CPC ..... A61M 5/5086; A61M 5/142; A61M 5/14; A61M 5/16827; A61M 5/26831; A61M 5/16854; A61M 5/16859; A61M 2205/14; A61M 2005/16863; A61M 2005/16868; A61M 2005/16872; A61M 1/1098; A61M 2005/3128; A61M 5/488; A61M 5/482; A61M 5/48; A61M 5/484; A61M 1/365; A61M 1/3643; A61M 1/288; A61M 2005/1402

See application file for complete search history.

(56) References Cited

U.S. PATENT DOCUMENTS

| | | | |
|---|---|---|---|
| 5,496,273 A * | 3/1996 | Pastrone | A61M 5/142 604/67 |
| 2005/0107923 A1* | 5/2005 | Vanderveen | G05D 7/0629 700/282 |
| 2006/0042635 A1 | 3/2006 | Niklewski et al. | |
| 2011/0046477 A1 | 2/2011 | Hulvershorn et al. | |

FOREIGN PATENT DOCUMENTS

WO WO-2012/094348 A2 7/2012

* cited by examiner

*Primary Examiner* — Kami A Bosworth
*Assistant Examiner* — Nilay Shah
(74) *Attorney, Agent, or Firm* — Fred C. Hernandez; Mintz Levin Cohn Ferris Glovsky and Popeo, P.C.

(57) ABSTRACT

A patient care system is configured for infusing fluid to a patient. The system includes a plurality of fluid infusion pumps, each of which is connected to a respective fluid supply for pumping the contents of a fluid supply to a patient via fluid supply lines. The system includes a pressure sensor downstream of the fluid infusion pumps for determining if a particular fluid is connected to a designated infusion pump.

14 Claims, 4 Drawing Sheets

SYSTEM AND METHOD FOR VERIFYING ALIGNMENT OF DRUG PUMP AND FLUID SUPPLY

BACKGROUND

A hospital patient often has the need for multiple intravenous (IV) infusions from multiple supplies of fluids, such as drugs. This requires the use of multiple infusion pumps that are connected to the patient and to fluid containers via fluid lines. As a result, the multiple fluid lines often become tangled or unruly.

A nurse or medical practitioner is required to trace the fluid line from the container to the patient to ensure the correct drug is infusing through the correct pump and connected to the correct catheter. However, as additional fluid supplies are used in the system, the fluid lines can get intertwined. This makes it difficult for the nurse to quickly and efficiently trace the fluid lines to the proper pump and fluid supply, especially in the region of the fluid line downstream or below the pump. A nurses may begin tracing the line, reach a point where several lines are crossed or tangled, and proceed to select the wrong line as a result of the confusion of sorting through several intertwined lines. A serious error may occur if a line is connected incorrectly to a pump, such as an epidural line connected to an IV line. Or two lines can be connected together that are not compatible.

In view of the foregoing, there is a need for methods and devices for properly sorting through fluid lines in an infusion system.

SUMMARY

Disclosed is a method for verifying that a particular fluid supply is connected to a pump mechanism wherein the pump mechanism acts on a fluid conduit coupled to the fluid supply to control movement of fluid from the fluid supply through the fluid line, the method comprising: causing an operator-induced pressure change in the fluid line at a downstream portion of the fluid line located between the pump mechanism and a patient; sensing pressure in the downstream portion of the fluid line; detecting the operator-induced pressure change in the downstream portion of the fluid line and indicating a connection verification that the fluid supply is connected to the pump mechanism upon detection of the operator-induced pressure change.

Further disclosed is a patient care system for infusing multiple medical fluids, the patient care system comprising: a plurality of fluid containers each adapted to hold a separate medical fluid; a plurality of fluid lines each in fluid communication with a separate fluid container from among the plurality of fluid containers; a plurality of pump channels each adapted to receive and connect to a separate fluid line from among the plurality of fluid lines and to operate on the received conduit to pump the fluid from the fluid container connected to the received conduit; a plurality of pressure sensors each associated with a pump channel, each coupled to a separate fluid line from among the plurality of fluid lines, and each located downstream of the associated pump channel providing the sensor signals representative of pressure in the fluid line with which the pressure sensor is coupled; and a processor connected to the plurality of pressure sensors and to the plurality of pump channels, the processor configured to verify that a particular fluid container from among the plurality of fluid containers is connected to a particular pump channel from among the plurality of pump channels, wherein the processor has a connection verification mode in which the processor is configured to monitor the pressure signals for a predetermined time period to detect an operator-induced pressure change and to provide a verification indication when the processor receives pressure signals indicative of the operator-induced pressure change in a particular conduit to thereby verify that the particular fluid container is connected to the particular pump channel through the particular conduit.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

Like reference symbols in the various drawings indicate like elements.

DETAILED DESCRIPTION

Disclosed is a patient care system for infusing fluid to a patient. The system includes a plurality of fluid infusion pumps, each of which is connected to a respective fluid supply for pumping the contents of a fluid supply to a patient via fluid supply lines. The system includes a pressure sensor downstream of the fluid infusion pumps for determining if a particular fluid is connected to a designated infusion pump.

Figure 1:
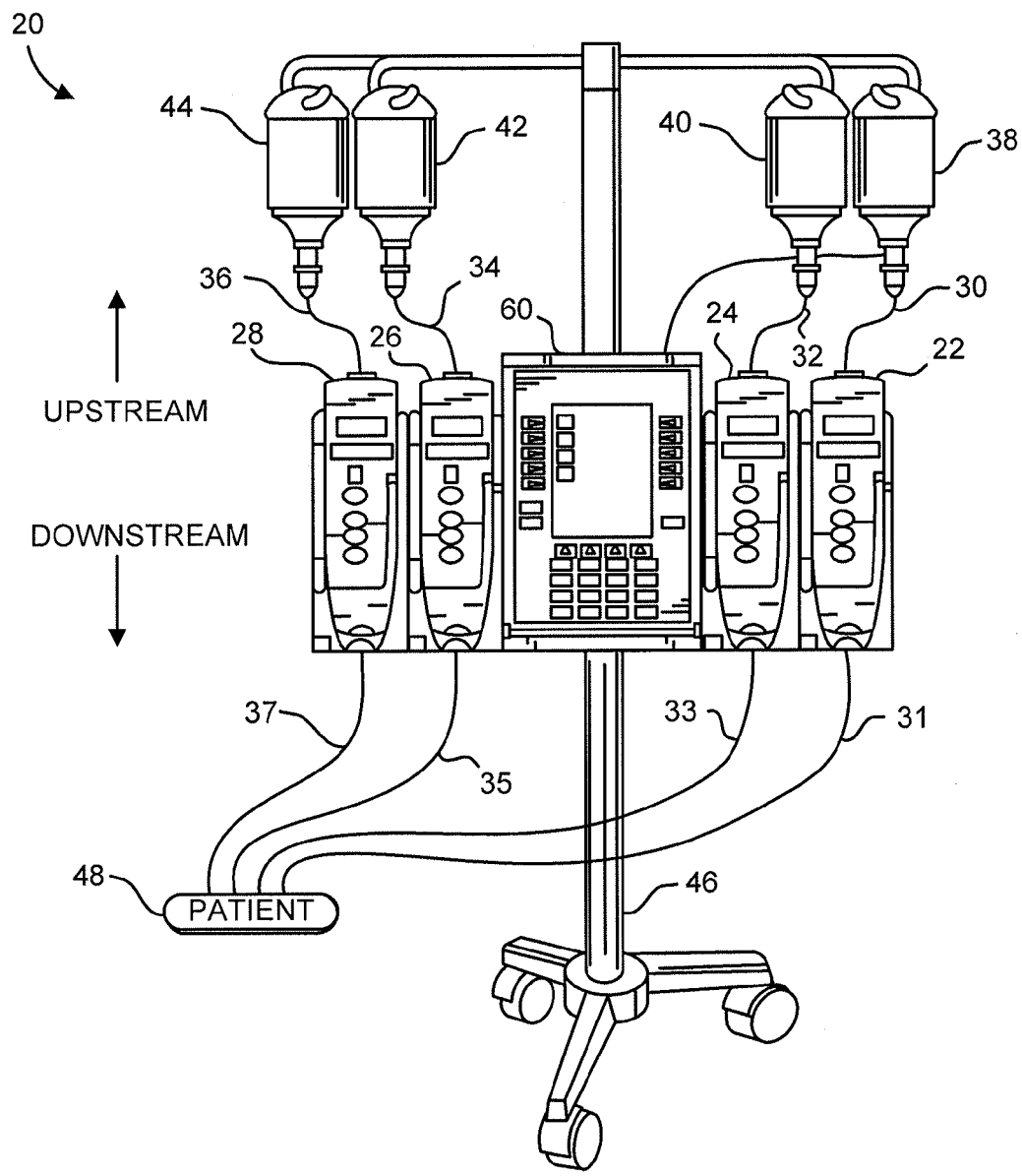
FIG. 1 is a front view of a patient care system having four fluid infusion pumps, each of which is connected to a respective fluid supply for pumping the contents of the fluid supply to a patient.

Referring now in more detail to the drawings in which like reference numerals refer to like or corresponding elements among the several views, there is shown in FIG. 1 a patient care system 20 having four infusion pumps 22, 24, 26, and 28 each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as tubing, through which fluid can flow through.

Fluid supplies 38, 40, 42, and 44, which may take various forms but in this case are shown as bottles, are inverted and suspended above the pumps. Fluid supplies may also take the form of bags or other types of containers. Both the patient care system 20 and the fluid supplies 38, 40, 42, and 44 are mounted to a roller stand or IV pole 46.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other.

Typically, medical fluid administration sets have more parts than are shown in FIG. 1. Many have check valves, drip chambers, valved ports, connectors, and other devices well known to those skilled in the art. These other devices have not been included in the drawings so as to preserve clarity of illustration.

It is generally desirable to verify the correct connection of each fluid supply 38, 40, 42, and 44 to the correct pump 22, 24, 26, and 28 prior to activating the pumping mechanism of a pump so that a fluid is not infused into the patient with incorrect pumping parameters. In this regard, a medical practitioner may desire to verify that the correct upstream fluid line 30, 32, 34, or 36 is connected to the correct pump pump 22, 24, 26, or 28. Or the medical practitioner may desire to verify that the correct downstream fluid line 31, 33, 35, or 37 is connected to the correct pump 22, 24, 26, or 28. Either of these may be done by a pressure sensor configuration that is coupled to fluid lines either upstream or downstream of the infusion pumps, as described in detail below.

It should be noted that the drawing of FIG. 1 is not to scale and that distances have been compressed for the purpose of clarity. In an actual setting, the distance between the bottles 38, 40, 42, and 44 and the infusion pump modules 22, 24, 26, and 28 could be much greater. There would be more of an opportunity for the upstream fluid lines 30, 32, 34, and 36 to become intertwined with each other when all four are dangling from the bottles, which can cause confusion as to which tube should be in which infusion module. The opportunity for confusion increases as the number of tubes increases.

Figure 2:
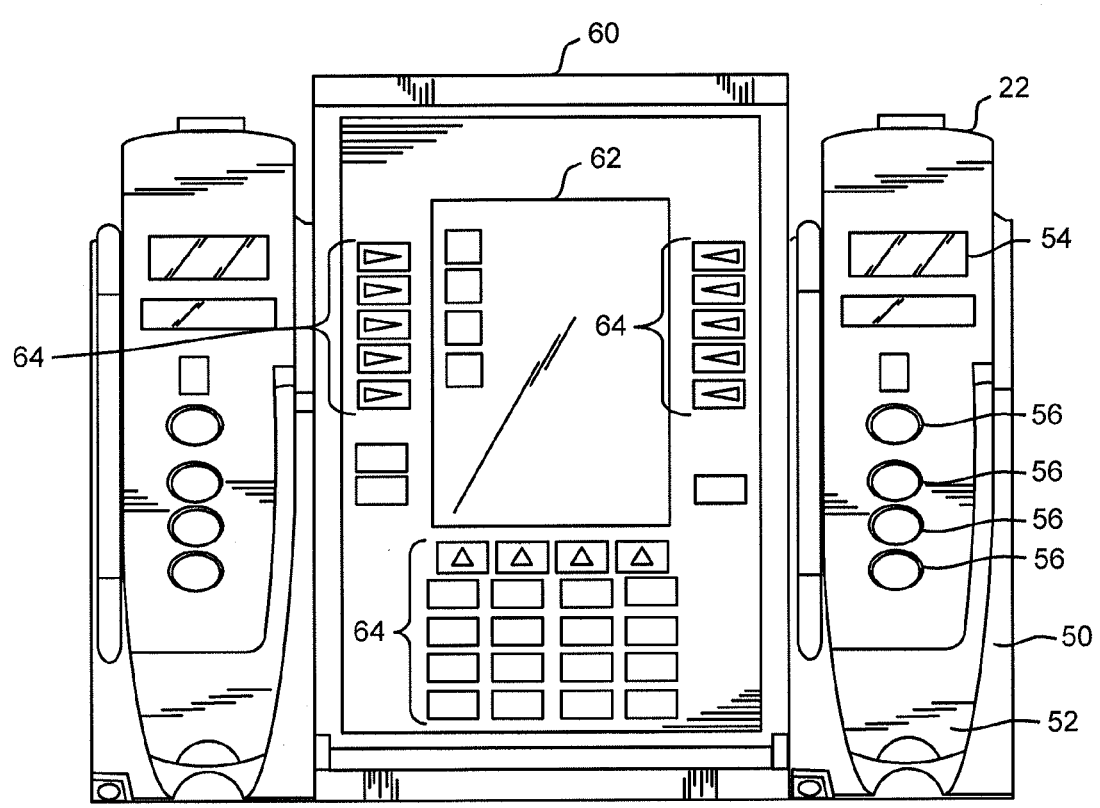
FIG. 2 is an enlarged view of a portion of the patient care system of FIG. 1 showing two of the fluid infusion pumps mounted at either side of a programming module, and the displays and control keys of each, with the programming module being capable of programming both infusion pumps.

Referring now to FIG. 2, an enlarged view of the front of the infusion pump 24 is shown. The pump includes a front door 50 and a handle 52 that operates to lock the door in a closed position for operation and to unlock and open the door for access to the internal pumping and sensing mechanisms and to load administration sets for the pump. When the door is open, the tube can be connected with the pump, as will be shown in FIG. 3. When the door is closed, the tube is brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages). Control keys 56 exist for programming and controlling operations of the infusion pump as desired. The infusion pump 24 also includes audio alarm equipment in the form of a speaker (not shown).

In the embodiment shown, a programming module 60 is attached to the left side of the infusion pump 24. Other devices or modules, including another infusion pump, may be attached to the right side of the infusion pump 24, as shown in FIG. 1. In such a system, each attached pump represents a pump channel of the overall patient care system 20. In one embodiment, the programming module is used to provide an interface between the infusion pump 24 and external devices as well as to provide most of the operator interface for the infusion pump 24.

The programming module 60 includes a display 62 for visually communicating various information, such as the operating parameters of the pump 24 and alert indications and alarm messages. The programming module 60 may also include a speaker (shown in FIG. 4) to provide audible alarms. The programming module also has various input devices in this embodiment, including control keys 64 and a bar code scanner (not shown) for scanning information relating to the infusion, the patient, the care giver, or other. The programming module also has a communications system (not shown) with which it may communicate with external equipment such as a medical facility server or other computer and with a portable processor, such as a handheld portable digital assistant ("PDA"), or a laptop-type of computer, or other information device that a care giver may have to transfer information as well as to download drug libraries to a programming module or pump.

The communications system may take the form of a radio frequency ("RF") (radio frequency) system, an optical system such as infrared, a Blue Tooth system, or other wired or wireless system. The bar code scanner and communications system may alternatively be included integrally with the infusion pump 24, such as in cases where a programming module is not used, or in addition to one with the programming module. Further, information input devices need not be hardwired to medical instruments, information may be transferred through a wireless connection as well.

FIG. 2 includes a second pump module 26 connected to the programming module 60. As shown in FIG. 1, more pump modules may be connected. Additionally, other types of modules may be connected to the pump modules or to the programming module.

Figure 3:
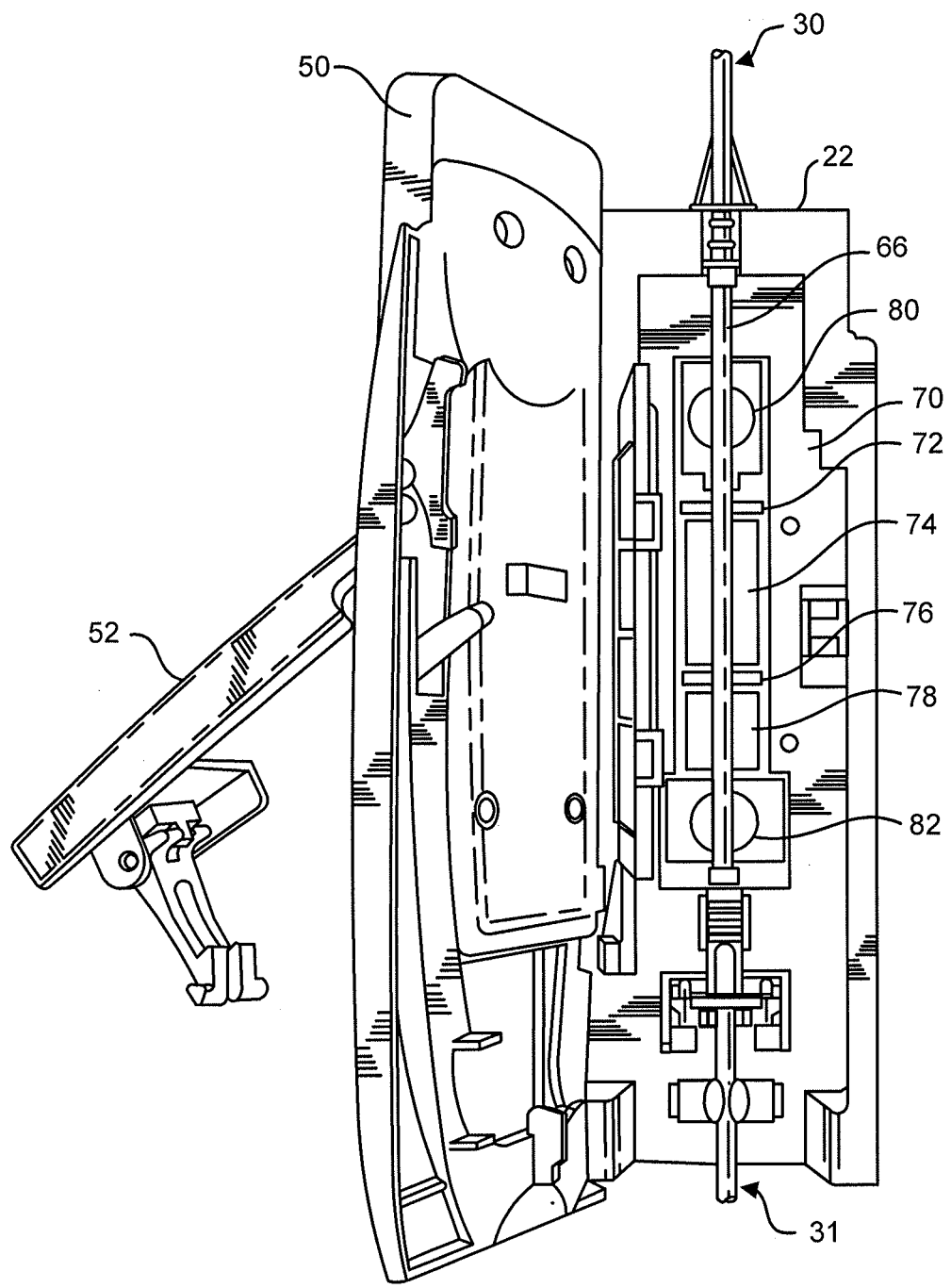
FIG. 3 is a perspective view of one of the fluid infusion pumps of FIGS. 1 and 2 with its front door in the open.

Turning now to FIG. 3, an infusion pump 22 is shown in perspective view with the front door 50 open, showing the upstream fluid line 30 and downstream fluid line 31 in operative engagement with the pump 22. The infusion pump 22 directly acts on a tube 66 that connects the upstream fluid line 30 to the downstream fluid line 31 to form a continuous fluid conduit, extending from the respective fluid supply 38 (FIG. 1) to the patient 48, through which fluid is acted upon by the pump to move fluid downstream to the patient. Specifically, a pumping mechanism 70 acts as the flow control device of the pump to move fluid though the conduit.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIG. 3 further shows a downstream pressure sensor 82 included in the pump 22 embodiment at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 1) and the flow control device, so that the connection of the correct fluid supply with the correct pump may be verified before any fluid is pumped to the patient.

With reference still to FIG. 3, an upstream pressure sensor 80 may also be included in the pump 22. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 1) and the flow control device, so that the connection of the correct fluid supply with the correct pump may be verified before any fluid is pumped to the patient.

Figure 4:
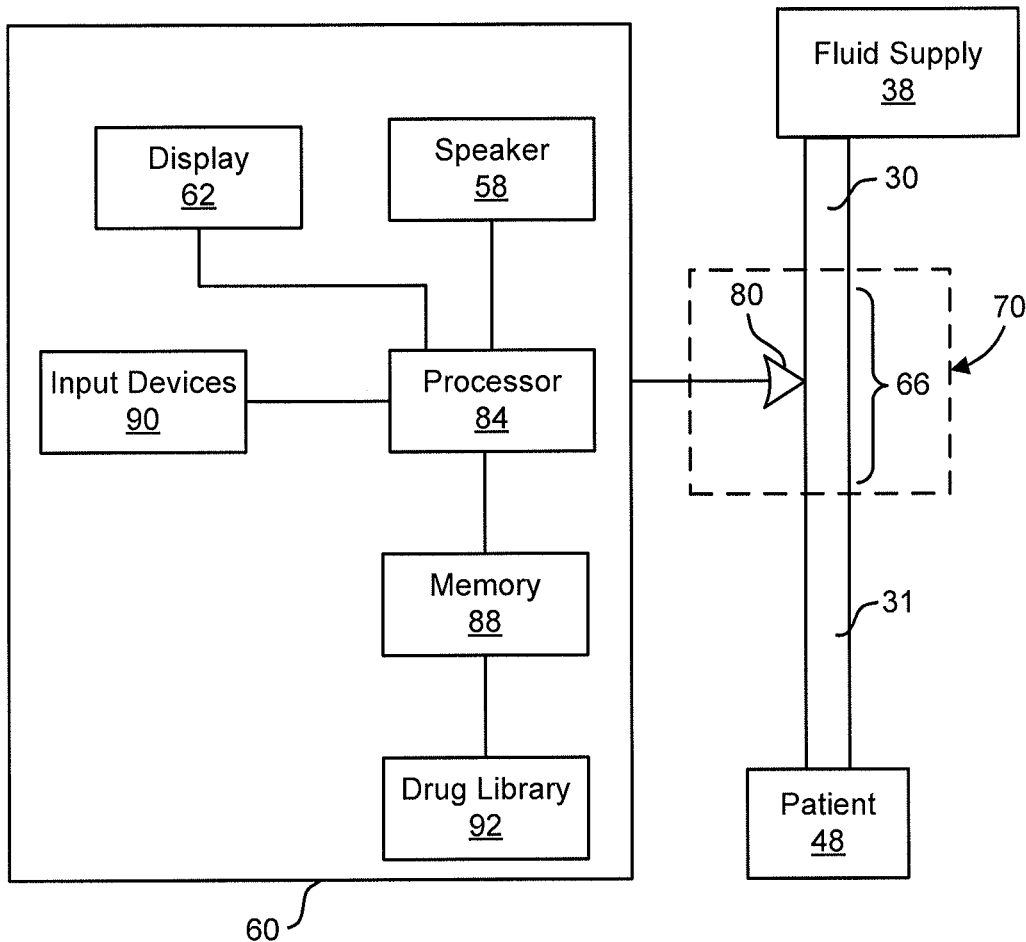
FIG. 4 is a block diagram showing components of one embodiment of the patient care system for verifying that the correct fluid source is connected to a pump.

Referring now to FIG. 4, the downstream pressure sensor 82 is shown coupled to the fluid conduit 66, as ordinarily occurs when the fluid conduit is loaded into the pump 22 and the pump door is closed (FIG. 1). The fluid conduit interconnects the fluid supply 38 with the patient 48 and provides a conduit for the fluid of the fluid supply to be infused into the patient.

The downstream pressure sensor 82 may take many forms well known to those skilled in the art, including a piezoresistive device. Consequently, no further technical details concerning the mechanical formation of the sensor are presented herein. The sensor 82 provides pressure signals in response to pressure sensed in the downstream fluid line 31. Those pressure signals are analog in form and are converted to digital form by an analog-to-digital converter ("A/D") integral with the sensor or by an A/D located elsewhere in the data stream. The digital pressure signals are supplied to a processor 84. In accordance with its programming, the processor is configured to receive the digital pressure signals and process them to detect pressure levels and pressure changes. In accordance with an aspect of the invention, the processor will be configured to detect a pressure change within a selected time period in order to determine if the correct fluid supply is connected with the pump and its associated pressure sensor. In the latter operation, the processor is referred to as running a connection verification mode.

Although FIG. 4 shows an embodiment in which the processor 84 is connected with a single pump or flow control device 70, it should be understood that other embodiments may exist in which multiple pump channels associated with a multi-channel patient care system may be monitored by the same processor. In such an embodiment, the processor performs the same functions for each pump channel of the system. As an example, FIG. 1 shows a four pump system in which the four pumps 22, 24, 26, and 28 are connected to a common programming module 60 having an internal processor. The processor of the programming module 60 may perform the "connection verification mode" for all four pumps.

The processor 84 has a connection verification mode in which it delays the flow control device 70 from moving fluid through the conduit 66 to the patient 48 until the processor verifies that the correct downstream fluid line 31 is connected to the pump. This is done by the processor detecting a purposely induced pressure change in the upstream conduit. In determining if a pressure change has occurred, the processor may be configured to detect a pressure change that exceeds a minimum threshold in one embodiment. In another embodiment, the processor may be further configured to detect an appropriate pressure decay response subsequent to a detected pressure change.

Thresholds or other reference values for evaluating whether the induced pressure change has in fact occurred in the conduit connected with the pump may be stored in a memory 88 which the processor 84 can access. The programs of the processor, including the program supporting the connection verification mode, may be stored in the same memory 88, or in another memory (not shown). Use of memory to store programs and data is well known and no further details are provided here. Values and other programming may also be input into the memory using an input device 90, such as control keys, or may be preprogrammed.

In one embodiment of the connection verification mode, the processor 84 is configured to begin its connection verification mode when it senses the existence of a fluid conduit 66 connected to the pump. Sensing the existence of a fluid conduit connected to the pump may be performed in different ways, such by detecting a change in the pressure signals from either the upstream or downstream pressure sensors, or by other means. Once the processor senses that the door 50 of the pump has been closed and the door handle 52 locked, the processor will then await the programming of the pump for operating parameters, such as flow rate, an identification of the drug being infused, and possibly other parameters. The latter manual programming step may not be necessary if the pump has been automatically programmed, such as by use of a bar code reader that was used to input pump operating parameters from a bar code label mounted to the fluid supply.

Once the processor 84 determines that the pump 70 has been loaded with an upstream fluid line 30 and the pump has been programmed for operation, the processor will then request the operator of the pump to induce a pressure change in the downstream line 31 that should be connected to the infusion pump. The operator may induce a pressure change in the downstream line in a variety of manners. For example, the operator may pinch or kink the downstream fluid line 31, or the operate may close a clamp on the downstream fluid line 31.

Figure 5:
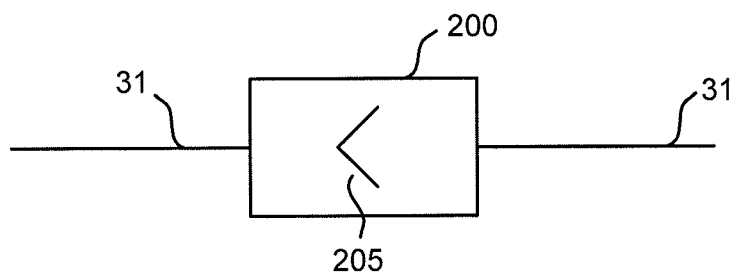
FIG. 5 is a flow chart depicting one embodiment of a method incorporating aspects of the present invention, for verifying that the correct fluid source is connected to a pump.

In another embodiment, shown in FIG. 5, a collapsible reservoir 200 is positioned along the downstream fluid line 31 (or any of the downstream fluid lines 33, 35, and/or 37). The reservoir defines an internal chamber that communicates with the internal lumen of the downstream fluid line 31 such that pressure changes in the chamber of the reservoir 200 are communicated through the downstream fluid line. A nurse can squeeze or otherwise collapse the reservoir 200 to cause a pressure change in the reservoir that is communicated to the downstream pressure sensor 82 via the downstream fluid line 31. A one-way valve 205 may be positioned inside the reservoir. The one way valve 205 is configured to close in the downstream direction (i.e. prohibit fluid flow toward the patient) upon collapse or squeezing of the reservoir 200. The valve 205 acts as a safety feature that prevents fluid from unintentionally being pushed toward the patient when the reservoir 200 is squeezed.

In an alternative embodiment, the processor may suggest such ways to induce the required pressure change through a visual text or graphics indication on the display 62 of the programming module 60. Because the downstream pressure sensor 82 is located downstream of the pumping mechanism 70, it can continually monitor the pressure existing in the downstream fluid line 31 and can detect induced pressure changes. The processor thus controls the downstream pressure sensor to the "on" mode and continually monitors the pressure signals it provides. If the operator squeezes the correct reservoir 200, i.e. the one connected to the conduit mounted to the pump, an increase in pressure in the conduit will be sensed by the downstream sensor, and by the processor, and the correct fluid supply for the pump will have been verified.

Once the processor has instructed the operator to induce the pressure change, the processor will then wait for a predetermined period of time within which it expects to receive pressure signals indicating that the requested pressure change has been induced. During the predetermined period of time during which the processor is waiting to receive the induced pressure change, the processor inhibits or delays the flow control device 70 from moving fluid through the conduit 66. The predetermined time period may be set at fifteen seconds for example, or a different time period. During the time period, the processor may display an appropriate indication such as "WAITING FOR OPERATOR-INDUCED PRESSURE CHANGE" or "SQUEEZE DOWNSTREAM RESERVOIR TO VERIFY CORRECT SET LOADING" or other message, so the operator can immediately see what mode the processor and pump are in.

In yet other aspects, a processor that monitors multiple pumping channels may be programmed to look for a pressure change in any of the downstream channels when it prompts the operator to induce a pressure change in one channel. By this technique, the processor can then indicate to the operator in which downstream channel the pressure change was actually detected. If the pressure change occurred in a channel other than the channel in which it was expected, the processor may indicate a misloading of the channel, but time will be conserved in that the processor may also indicate to the operator through a front panel display or through other means which channel in fact has the desired conduit. The operator can then quickly locate that conduit and place it in the correct channel.

If during the predetermined period of time within which the induced pressure change should occur no pressure change is received by the processor from the pump, the processor will then query the operator through the display or by other means to ask if the operator has induced a pressure change. An audio attention alert, such as a short audible beep, may also be provided to audibly alert the operator that the processor is making a query. If the operator responds that the pressure change has been induced, the processor will indicate that no pressure change was sensed in the right pump. Such an indication may result if the downstream fluid line in which the pressure change was induced is not connected to the right pump 22. As a result, the processor may display a "wrong conduit" alert indication visually on the display 54 of the infusion pump 22 and an audible alarm from the speaker of the pump. The alert indication may also be provided on the display 62 and/or speaker 58 of the programming module 60.

If the operator responds that a pressure change has not yet been induced, the processor may begin a new time period in which it waits for an induced pressure change. The new time period may be the same as the preceding time period or it may be different. In another embodiment, the processor may switch to a "suspend" mode in which it suspends further operation until the operator presses a particular key, such as the ENTER key as one of the input devices 90, at which time, the processor will once again enter a time period of the verification mode in which it monitors for an induced pressure change.

If the processor 84 detects the induced pressure change within the predetermined time period, the processor may provide a verification indication on displays 54 (FIG. 2) or 62 and then terminate the delay of operation of the flow control device 70. That is, the processor no longer inhibits pump operation but instead, allows the pump to begin pumping at the initiation of the operator. After any further programming of the pump is completed, such as by pressing the START key, the processor will control the flow control device to begin the infusion and move fluid through the fluid conduit 66 to the patient 48. Because operation of the flow control device is delayed until the processor detects the manually induced pressure change, the processor thereby verifies that the correct fluid conduit is connected to the correct flow control device prior to delivering the fluid to the patient.

Further detail on the connection verification mode of operation will now be described. In reference to FIGS. 1 through 4, a nurse begins the process by hanging a bag 38 of medication from a stand, such as the roller stand 46 shown in FIG. 1, priming the fluid line 30 with the fluid from the fluid supply to be infused into the patient 48. If the fluid supply has a bar code label, or other information device, containing pump operating parameters, the nurse may read it into the pump through a bar code reader, infrared transfer, or other means to automatically program the pump. The conduit is connected to the pump and if automatic programming of the pump has not occurred, the nurse may manually program the pump through the use of the control keys 56 or 64, for example.

The nurse may also use the control keys 64 on the programming module 60 to select a drug from a data base of drugs stored in a drug library 92 (FIG. 4), the drug library being stored in the memory 88 of the patient care system 20. In one embodiment, the drug library is stored in the memory of the programming module 60 (FIG. 2) and a scrolling list of drugs may be displayed on the display 62 of the programming module 60 (FIG. 2) for selection. The drug library may also include flow rates, doses, and other information that can be selected and which represents the best practices of the clinic in which the pump is located. In a further system, the programming module, infusion pump, or other processing device may contain a drug library having drug names and accepted best practices of the clinic for administration of that drug.

Before a pump is allowed to infuse a drug into a patient, the processor is also configured through programming to check the pump's programming against the drug library 92. The drug library may also include pumping limits and in one case, "soft" limits may exist. If the operator of the pump were to select a pumping parameter that is outside a "soft" limit, a "soft" alert may be provided by the processor to the operator as an indication that he or she has programmed a parameter that is outside a limit. However, a "soft" limit can be overridden by the operator and pumping may be commenced. The drug library may also include "hard" limits. If the operator of the pump were to select a pumping parameter that is outside a "hard" limit, a "hard" alert may be provided by the processor to the operator as an indication that he or she has programmed a parameter that is outside a hard limit. A "hard" limit cannot be overridden by the operator and pumping will not be permitted until the programmed parameter is changed to an acceptable level. Such a system providing limits and alerts through a drug library is available through the GUARDRAILS system from CAREFUSION, Inc. The drug library of the patient care system may be configured to be periodically updated through the communications system using an external device such as a computer running appropriate software.

In an embodiment, the drug library 92 may also include drug entries linked to an instruction that the processor controlling a flow control device is to run the connection verification mode. In particular, selected drugs may include such an instruction in addition to dosages, and pumping parameters. This approach would automatically put the processor in the connection verification mode without further operator input. Therefore, once an operator enters a drug name that is in the library, and if that drug name includes a link to instruct the processor to run the connection verification mode, the processor will automatically begin the verification mode.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A method for verifying that a particular fluid supply is connected to a pump mechanism wherein the pump mechanism acts on a fluid line coupled to the fluid supply to control movement of fluid from the fluid supply through the fluid line, the method comprising:
    causing an operator-induced pressure change in the fluid line at a downstream portion of the fluid line located between the pump mechanism and a patient, wherein a collapsible reservoir is positioned entirely external of the pump mechanism and located in the downstream portion of the fluid line entirely downstream of the pump mechanism, and wherein causing the operator-induced pressure change comprises squeezing the reservoir, wherein the reservoir includes a one-way valve that inhibits fluid flow toward the patient when a pressure change occurs in the reservoir;
    sensing pressure in the downstream portion of the fluid line;
    detecting the operator-induced pressure change in the downstream portion of the fluid line and
    indicating a connection verification that the fluid supply is connected to the pump mechanism upon detection of the operator-induced pressure change.

2. The method of claim 1, wherein causing the operator-induced pressure change comprises kinking the downstream portion of the fluid line.

3. The method of claim 1, further comprising generating a pressure signal representative of the pressure in the downstream portion of the fluid line.

4. The method of claim 1, further comprising delaying the pump mechanism from moving fluid through the fluid line until the pressure change in the fluid line is detected.

5. The method of claim 1, further comprising detecting the operator-induced pressure change at a second pump mechanism; and indicating an identity of the second pump mechanism.

6. The method of claim 1, further comprising prompting an operator to confirm that a pressure change has been induced if the induced pressure change is not detected within a predetermined time period.

7. The method of claim 1, further comprising prompting an operator to squeeze the downstream portion of the fluid line.

8. The method of claim 1, further comprising prompting an operator to squeeze the collapsible reservoir.

9. A patient care system for infusing multiple medical fluids, the patient care system comprising:
- a plurality of fluid containers each adapted to hold a separate medical fluid;
- a plurality of fluid lines each in fluid communication with a separate fluid container from among the plurality of fluid containers;
- a plurality of pump channels each adapted to receive and connect to a separate fluid line from among the plurality of fluid lines and to operate on a received fluid line to pump a fluid from the fluid container connected to the received fluid line;
- a plurality of pressure sensors each associated with a pump channel, each coupled to a separate fluid line from among the plurality of fluid lines, and each located downstream of the associated pump channel providing sensor signals representative of pressure in the fluid line with which the pressure sensor is coupled;
- a plurality of collapsible reservoirs, each entirely external to a pump mechanism and coupled to a downstream portion of a corresponding fluid line entirely downstream of a pump mechanism, each collapsible reservoir including a one-way valve that regulates fluid flow toward a patient; and
- a processor connected to the plurality of pressure sensors and to the plurality of pump channels, the processor configured to verify that a particular fluid container from among the plurality of fluid containers is connected to a particular pump channel from among the plurality of pump channels, wherein the processor has a connection verification mode in which the processor is configured to monitor the pressure signals for a predetermined time period to detect an operator-induced pressure change and to provide a verification indication when the processor receives the pressure signals indicative of the operator-induced pressure change in a particular fluid line to thereby verify that the particular fluid container is connected to the particular pump channel through the particular fluid line.

10. The patient care system of claim 9, wherein the processor is further configured to delay a pump channel from moving fluid through the respective fluid line until the processor receives the pressure signals indicative of the operator-induced pressure change in the respective fluid line.

11. The patient care system of claim 9, wherein the processor in the connection verification mode is configured to detect that the operator-induced pressure change is at any of the pump channels with which the processor is connected and indicate an identity to an operator of the pump channel at which the operator-induced pressure change was actually detected.

12. The patient care system of claim 9, wherein the processor in the connection verification mode is further configured to prompt an operator to induce a pressure change in the particular fluid line.

13. The patient care system of claim 9, wherein the processor in the connection verification mode is further configured to: prompt an operator to confirm that a pressure change has been induced if the operator-induced pressure change is not detected within a predetermined time period.

14. The patient care system of claim 9 further comprising a drug library in which is stored a data base of drugs, wherein the drug data base also includes instructions linked to selected drugs to instruct the processor to run the connection verification mode; and an input device coupled to the processor by which a selection of a drug from the drug data base is made; wherein the processor receives the drug selection from an input device, accesses the drug library, and is configured in the connection verification mode in event that such an instruction is linked to the selected drug.

* * * * *